United States Patent [19]

Donovan

[11] Patent Number: 4,924,882

[45] Date of Patent: May 15, 1990

[54] ELECTRONIC CUSPOTOME AND METHOD OF USING THE SAME

[76] Inventor: Thomas J. Donovan, 110 Westland St., Manchester, Conn. 06040

[21] Appl. No.: 161,175

[22] Filed: Feb. 26, 1988

[51] Int. Cl.$^5$ .............................................. A61B 17/36
[52] U.S. Cl. ........................................ 128/898; 606/45
[58] Field of Search ....................... 128/303.14, 303.16, 128/305, 898, 303.15; 604/22; 606/45

[56] References Cited

U.S. PATENT DOCUMENTS 4,497,320 2/1985 Nicholson et al. ................... 128/305
4,658,820 4/1987 Kucek ............................ 128/303.14

FOREIGN PATENT DOCUMENTS 2851239 3/1980 Fed. Rep. of Germany .......................... 128/303.17

OTHER PUBLICATIONS

Leather, R. P. et al., "Experience with the Saphenous Vein Used in Situ for Arterial Bypass", *The American Journal of Surgery,* vol. 142 (Oct. 81), pp. 506–510.

*Primary Examiner*—Michael H. Thaler
*Assistant Examiner*—W. Lewis
*Attorney, Agent, or Firm*—Fishman, Dionne & Cantor

[57] ABSTRACT

A novel cuspotome comprised of a long, slender arm having a substantially transverse hook section which terminates at a rounded bulbous end is presented. A sharp knife edge, which faces inwardly of the hook section is adjacent to the bulbous end. With the exception of the lower inner arm of the knife edge and inner part of the bulbous end, the entire cuspotome is coated with an electrically insulative material, preferably a fluoropolymeric material. In accordance with the technique of the present invention, after insertion into a vein and positioned adjacent a venous valve, the novel cuspotome is provided with very short, pulsed exposures of adequate wattage to instantaneously divide the cusp. The present invention is particularly well suited for removing valves of the autograft or allograft saphenous vein for bypass of arterial obliterative disease.

6 Claims, 3 Drawing Sheets

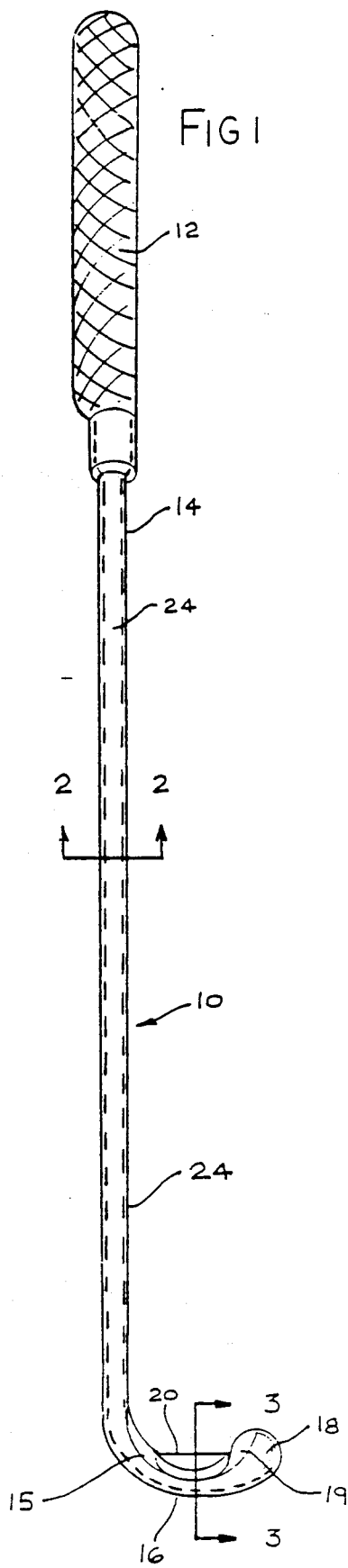
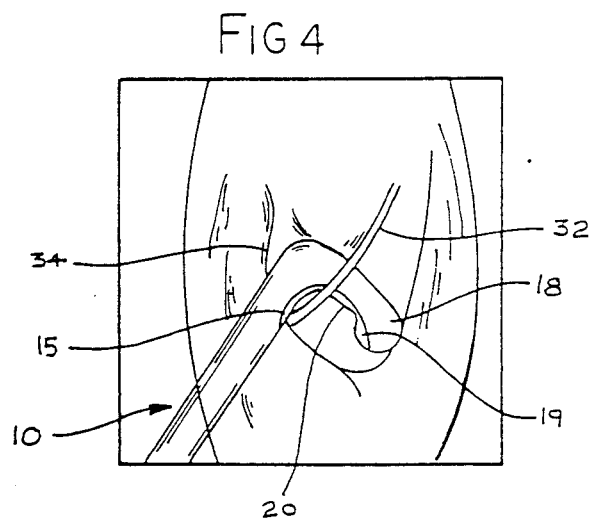
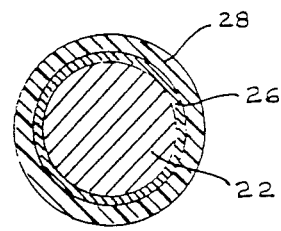
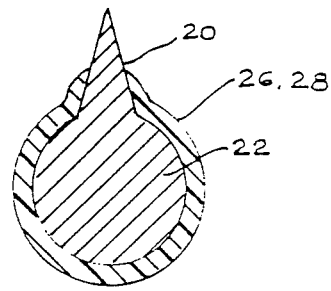

ELECTRONIC CUSPOTOME AND METHOD OF USING THE SAME

BACKGROUND OF THE INVENTION

This invention relates to a technique for valve incision and a novel valvulotome for practicing this technique. More particularly, this invention relates to a new and improved technique for incising venous valves using a small amount of current in conjunction with a hooked, retrocutting knife. This invention is particularly well suited for removing valves of the autograft or allograft vein for bypass of arterial obliterative disease.

In 1949 Kunlin described the first bypasses of femoral arterial obliterative disease with autogenous saphenous vein grafts. These were used in the reversed position to permit flow through the venous valves with central orientation. Because of the major discrepancies in size between the proximal and distal saphenous vein found in some patients, May et al in 1959 developed a technique for use of the vein in the nonreversed position with an olive-tipped inside stripper which bluntly disrupted the valves and some inner venous lining as well (see May AG, DeWeese JA, Rob CG: Arterialized in situ saphenous vein Arch Surg 1965;91:743–750). Hall first reported this in situ technique in 1961, but used multilevel transverse venotomies and excision of the leaflets (see Hall KV: The great saphenous vein used in situ as an arterial shunt after extirpation of the vein valves: A preliminary report. Surgery 1962;51:492–495). This was less traumatic but was slow and tedious and conducive to scarring and stricture in the smaller veins. Connolly, Harris et al performed the "in situ" operation in 1962 adapting the olive tipped inside stripper suggested by May for the intraluminal destruction of the leaflets (see Connolly JE, Harris EJ and Mills W: Autogenous in situ saphenous vein bypass of femoral-popliteal obliterative disease. Surgery 1964;55:144–153). Criticisms of the operation included the dangers of residual arteriovenous fistulas, trauma to the endothelium from the rough disruption of the valves and stenoses at the valve sites from residual uncut cusps or trauma. Samuels et al reported a new valvulotome, since then copied by many even to the present time. This was introduced upward from the distal end of the vein, destroying valve competency as it was withdrawn blindly (see Samuels PB, Plested WG, Haberfelde, GC, et al: in situ saphenous vein arterial bypass. Am Surg 1968;34 122-130). In 1973 Skagseth and Hall devised a similar instrument with a retrocutting edge substituting it for the multiple venotomy technique they had first introduced (see Skagseth E, Hall KV: in situ vein bypass: Experiences with new vein valve strippers. Scand J Thorac Cardiovasc Surg 1973;7:53–58). Even the present modifications of these retrograde valvulotomes, with blind and traumatic disruptions of the valves, fail to accomodate to anomalies in the venous anatomy or abrupt changes in the vein sizes.

The procedure fell into disrepute in the 1970's after late results showed graft failure primarily from endothelial trauma and inadequate management of the valve excision. In 1976 Mills introduced a hooked, retrocutting knife for coronary bypass grafts which emphasized atraumatic division of the cusp (see Mills NL and Ochsner JL: Valvotomy of valves in saphenous vein graft before coronary artery bypass. J Thorac Cardiovasc Surg 1976;71:878–879). It was inserted distally and on withdrawal, engaged the individual cusp which was slightly distended and identified with gentle retrograde perfusion from the proximal vein. In 1979, Leather, Karmody et al reappraised the in situ procedure with the concept of gentle division of the cusps and introduced microvascular scissors proximal to the valves (see Leather RP, Powers SR, and Karmody AM: A reappraisal of the in situ saphenous vein arterial bypass: Its use in limb salvage. Surgery 1979:453–461). This technique was difficult to apply to the distal vein where the branches were too small to accept the scissors. In 1981 Leather reported a miniaturized Mills knife introduced from below the valves through the vein end or a convenient distal branch (see Leather RP, Shah DM, et al: Further experience with the saphenous vein used in situ for 15 arterial bypass. Am J Surg 1981;142:506).

With new, more gentle manipulation of grafts, the results of the in situ grafts improved. In 1981, the inventor herein and others began using the in situ in the leg and the nonreversed (or orthograde) free grafts for coronary bypass and a variety of procedures throughout the vascular tree (see Donovan TJ and Lowe R: Biologic fate of valves in reversed and nonreversed arterial vein grafts. Am J Surg 1985; 148:435–440). However, it was noted that the Mills/Leather knives which cut fairly well when new, became dull with use and would either slip off and miss the cusp or disrupt it with undue force and trauma. While options are available for preserving the atraumatic technique, these options all suffer from important drawbacks and deficiencies. For example, one option was to buy the knives in bulk for about $30.00 each and consider them disposable. Another option was to resharpen the knives with jewelers instruments once or twice to maintain a relatively sharp edge. However, the knives now are resharpened too often until they become a blunt hook which is traumatic and ineffective. While it has been suggested to use obsidian or some other metal which would take and hold a sharper edge longer; unfortunately, such a knife edge would be very costly. A diamond knife has been developed which is sharp and cuts very easily. However, it is expensive (about $900) and eventually becomes dull with about 120 or more valvotomies or about 25 to 30 venous grafts.

In the 1920's, Dr. Harvey Cushing and Dr. W. T. Bovie developed a dual purpose electro-surgical unit for coagulation of bleeders and for cutting tissue. When the triode vacuum tube was invented, it was possible to produce current that was pure and easy to regulate. High frequency electrical current for pure cutting or coagulation is now used in about 80% of operating room procedures as well as in office practice of dermatology, gynecology, urology, proctology, oral surgery and other specialities. It is also used during cystoscopy with the electronic cutting accomplished in a liquid medium.

SUMMARY OF THE INVENTION

The above-discussed and other problems and deficiencies of the prior art are overcome or alleviated by the novel electronic cuspotome and method of using the same of the present invention. In accordance with the present invention, the cuspotome comprises a long, slender arm having a substantially transverse hook section which terminates at a rounded, bulbous end. A sharp knife edge, which faces inwardly of the hook, is adjacent the bulbous end. With the exception of the lower inner arm, the knife edge and inner part of the bulbous end, the entire knife is coated with an electrically insulative material which permits ease of movement within the vein. This insulative material is preferably a fluoropolymer such as Teflon.

The technique of the present invention utilizes the novel cuspotome in conjunction with very short, pulsed exposures of adequate wattage to instantaneously divide the cusp. An electric circuit is completed by immersing the free vein graft in a conductive solution (saline) in a stainless steel basin and by attaching a grounding electrode to the basin. The proximal vein is perfused gently in a retrograde manner with a non-conductive solution such as sorbitol/mannitol. It is also possible to retroperfuse the proximal vein graft anastomosed proximally to the patient's artery with a grounding plate attached to the patient to complete the electrical circuit in the generator.

The cuspotome and technique for using the same of the present inventions permit quick, easy, highly effective and low cost cuspotomes relative to prior art methods and cupotomes.

The above-discussed and other features and advantages of the present invention will be appreciated and understood by those skilled in the art from the following detailed description and drawings.

BRIEF DESCRIPTION OF THE DRAWINGS

Referring now to the drawings, wherein like elements are numbered alike in the several FIGURES:

FIG. 1 is a front elevation view of an electronic cuspotome in accordance with the present invention;

FIG. 2 is a cross-sectional elevation view along the line 2—2 of FIG. 1;

FIG. 3 is a cross-sectional elevation view along the line 3—3 of FIG. 2;

FIG. 4, is a perspective view of the electronic cuspotome of FIG. 1 dividing the cusp of a venous valve;

DESCRIPTION OF THE PREFERRED EMBODIMENT

Figure 5:
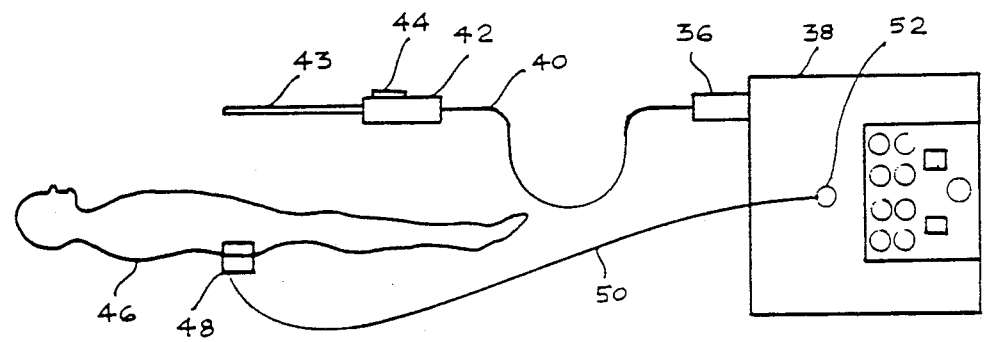
FIG. 5 is a schematic view of a first embodiment of an operational set-up using the cuspotome of FIG. 1.

Referring first to FIGS. 1 and 2, an electronic cuspotome in accordance with the present invention is shown generally at 10. Cuspotome 10 comprises an elongated handle 12, a long cylindrical arm 14 and a hooked end section 16. Hooked end section 16 extends laterally from arm 14 at substantially 90 degrees where it terminates at a rounded bulbous end 18. Hook section 16 further includes a sharp blade 20 facing in the direction of handle 12. As shown in FIGS. 2 and 3, cuspotome 10 is comprised of a conductive material 22, preferably metal such as steel. The steel is preferably sandblasted to provide a pitted surface. On this pitted surface is a layer of electrically insulative material 24 which should have a low coefficient of friction. In a preferred embodiment, the outer insulative covering is a fluoropolymer. Specifically, a green PTFE acid primer 26 is bonded to the steel 22 under high temperature and two or more coats of a clear PTFE resin 28 is then fused to the acid primer 26. These insulative layers 26 and 28 are then removed from the lower inner arm 15, the knife edge 20 and the inner bulbous end 19 to expose the metal and permit monopolar electrical contact with the tissue.

The operator holds the cuspotome with sterile rubber gloves to protect their fingers. The handle 12 is free of insulation and is used as an electrical contact wherein short, pulsed exposures of electrical current are made to cuspotome 12 for cutting of venous valves as will be discussed below.

Although laser therapy is effective on and stays in atheromata inside human arteries, it is not well contained by normal tissue and vessel wall. To avoid damage to adjacent venous wall, the application of cutting currents to valves should be done with very short ("pulsed") exposures of adequate wattage to instantaneously divide the cusp. Inadequate power over longer periods will "bleed off" into and damage surrounding tissue. Although laser coagulation of atheromata in vascular lesions is under current study, pure cutting electric current has not been developed or used for normal venous valves. It is believed that the fear of endothelial injury has dissuaded other investigators from using electric current in a vein. In other words, it has been believed in the past that the cutting current would disrupt and otherwise damage the vein. Perhaps, for that reason, there has been no previous discussions or investigations of the use of electrical current to cut venous valves. Therefore, the excellent results achieved by use of the technique of the present invention has been unexpected and surprising.

With the development of semiconductors and transistors in the 1960's, the precision of solid state circuitry was translated into pin-point cutting control and avoidance of injury to surrounding tissue. Using the pure cutting current of known electrosurgical generators and engaging the cusp 32 of the venous valve 34 with the teflon coated retrocutting knife as shown in FIG. 4, the uncoated knife blade 20 will instantaneously divide the cusp 32 at low current settings in the 30 to 50 watt range and with very brief touching of the uncoated knife handle 12 with the electrode carrying the cutting current.

With this type of cuspotomy, it is important to control and minimize the amount of electrical energy (joules) utilized. This is done with retroperfusion of non-conducting, isotonic solution such as sorbitol-mannitol solution from the proximal end of the vein graft gently distending the valves closed; and with slight retraction of the handle assuring good cusp contact with the knife edge. As the valve cusp is divided, the steel exposured on the inner surface of the ball tip of the hooked knife is designed to completely divide the cusp and cause it to slide through with immediate cessation of the current due to loss of monopolar tissue contact.

Figure 6:
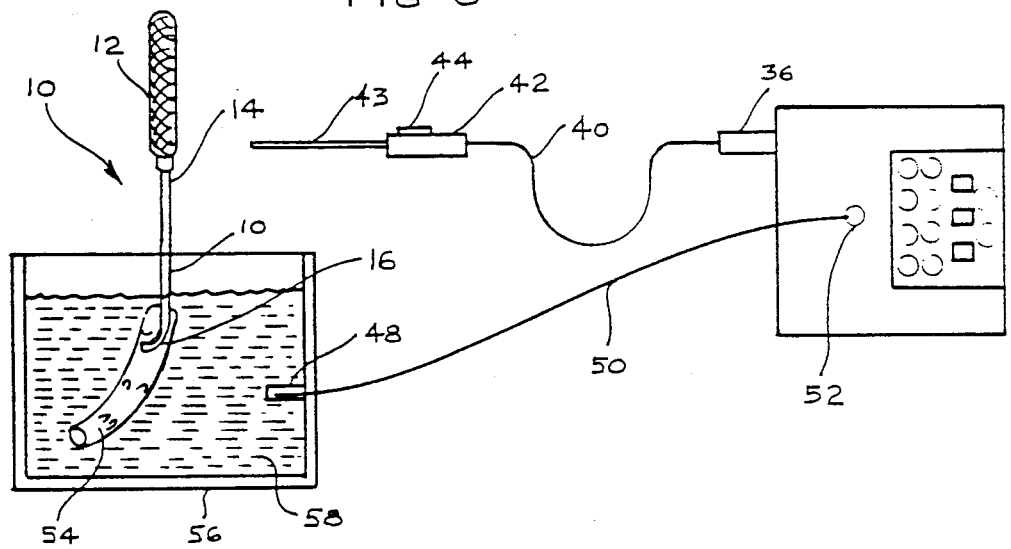
FIG. 6 is a schematic view of a second embodiment of an operational set-up using the cuspotome of FIG. 1.

Turning now to FIGS. 5 and 6, a known pulse timer 36 with a timing duration selector attached to a power unit 38 is preferably used into which will plug sterile wire 40 from an electrode handle 42 equipped with a switch 44. Depressing handle switch 44 will produce a short, pretimed pulse and by setting the generator dial at the lowest effective level, one can then measure, standardize and minimize the total electrical energy delivered that reliably divides the cusp.

FIGS. 5 and 6 show two alternative set-ups for practicing the present invention. In FIG. 5, the venous valves are cut while the vein remains in the patient 46. To accomplish this, an electrode 48 is attached to the patient's skin and connected by a wire 50 to a ground plug 52 on commercially available generator 38. Next, the cuspotome (not shown) is inserted into the vein, brought into contact with a cusp (as in FIG. 4) and the electrode rod 43 of electrode handle 42 is contacted with the metal handle 12 of the cuspotome 10. Upon depression of switch 44, a short electrical pulse will heat knife edge 20 to assist the sharp blade in making a quick and reliable division of the cusp. Note that the electrical circuit is completed through the patient's body and out through electrode plate 48 and grounding wire 50.

In FIG. 6, the vein 54 is actually removed from the patient and placed in a basin 56 filled with a conductive solution 58 such as saline. The same procedure as discussed with regard to FIG. 6 is then repeated to divide the valve cusps.

Experiments have been conducted with the vein graft surrounded by conductive fluids (as in FIG. 6) and in contact with the animal tissue and therefore the isolated grounding circuit (as in FIG. 5). In most experiments, a steel basin has been filled with normal saline with an attached grounding electrode to complete the isolated circuit and allow current flow. The vein, largely immersed in saline, is perfused in a retrograde fashion with sorbitol-mannitol solution to gently distend the vein and valve and assure good contact with the 10 knife edge and a 0.2 to 0.6 second exposure with about 40 watts uniformly divides the cusp. Gross inspection with a 10 to 40 power magnification from a dissecting microscope, has shown no damage to the vein wall adjacent to the valve with the 8 to 30 watt/second range for cuspotomy. The cusp is divided and partially eliminated with occasional, very slight browning of the cusp edge but no change is seen in adjacent wall. Light and electron microscopy studies are underway to evaluate the nearby endothelium of the venous sinus.

Figure 7:
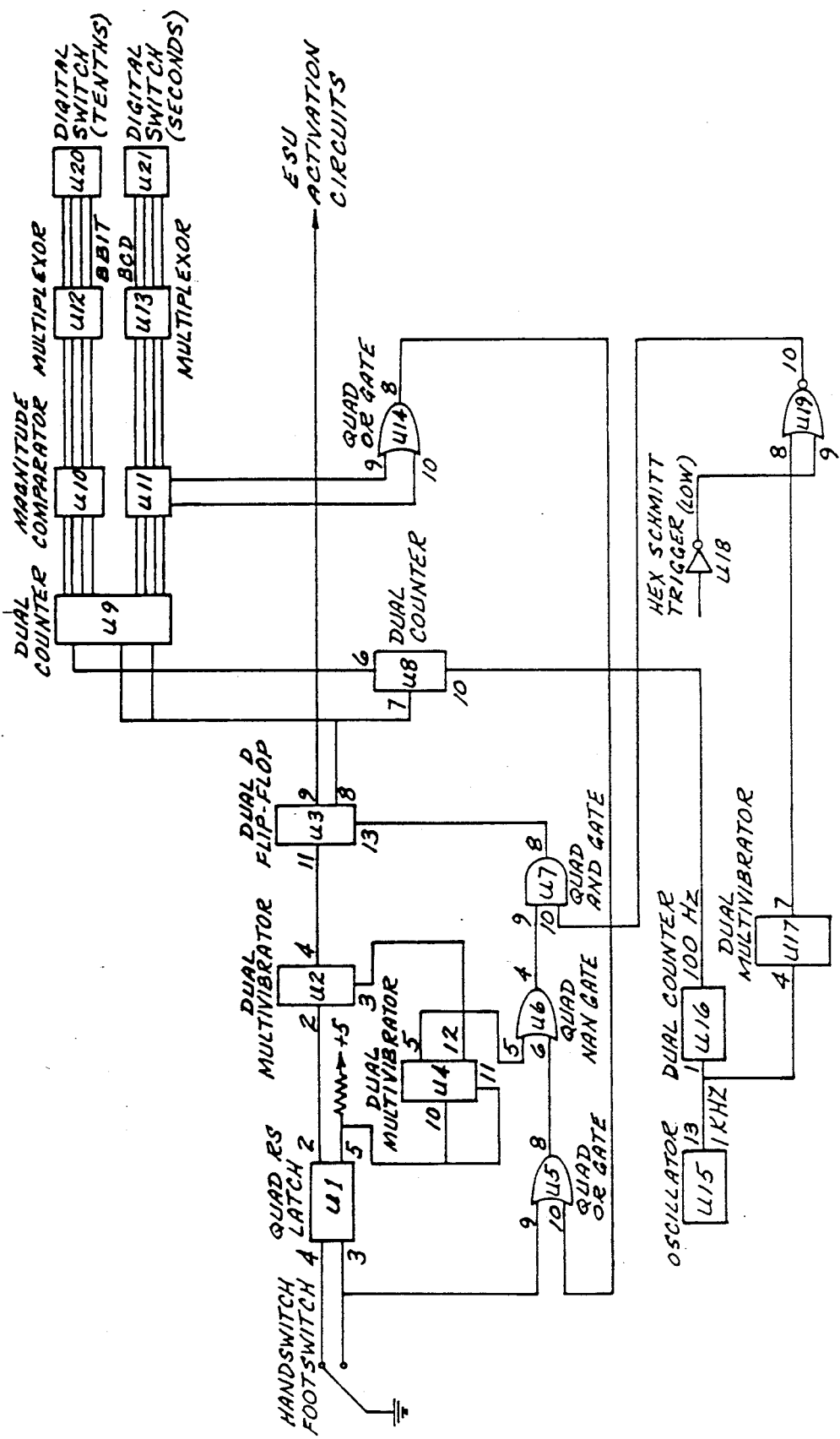
FIG. 7 is an electronic diagram of an external electrosurgical pulse duration control circuit for use with the cuspotome of FIG. 1.

As mentioned, the electrical generator 38 is commercially available, for example, Model SSE2K from Valley Lab of Boulder, Colo. and Model 3000A from Neomed of Boulder, Colo. The Pulse generator 36 may also be found commercially. However, in a preferred embodiment, pulse generator 36 includes the electronic circuit shown in FIG. 7.

The purpose of this circuit is to control the duration of cutting current output from an electrosurgical generator when such control is necessary to achieve a desired affect on tissue. Input to the circuit consists of a simple switch contact contained within handswitched active electrodes or external footswitches commonly associated with commercially available electrosurgical generators. Output from the circuit may require some additional modification depending on which generator the circuit is being interfaced to and how generator output is activated (i.e., digital logic vs. relay vs. closing of contacts within the generators own internal circuitry).

The circuit consists of four functional sections: (1) activation/deactivation control; (2) timing input; (3) pulse duration; and (4) clock function monitoring. The sequence of circuit function is as follows:

(1) Activation/Deactivation Control - When the handswitch or footswitch is closed, input to OR gate U5 goes low. Input from OR gate U14 is low (time-out has not yet occurred), thus the output from U5 and input to NAN gate U6 goes low, output from multivibrator U4 is used as a delay to allow confirmed positioning of the active electrode before generator power activation takes place. When the output from U4 goes low (e.g. after 2-3 seconds), then the output from U6 and the input to AND gate U7 goes high. Assuming clock function is satisfactory, the output NAN gate U19 will be high, and the output from U7 and input to flip-flop U3 will go high.

Concurrently with the above sequence when the handswitch or footswitch is closed, input to the RS latch U1 goes low and output to multivibrator U2 goes high. Activation delay through multivibrator U4 is initiated, and the U2 one-shot is triggered. The output from U2 goes high, thus clocking flip-flop U3 into the set state. The output from U3 activates the electrosurgical generator power output.

(2) Timing Input - Circuit timing signals are derived from the free running oscillator U15. The output from the oscillator, a 1K Hz square wave, is counted down to 100 Hz by counter U16 and down to 10 Hz by counter U8. The output of U8 provides the timing signal source to the pulse duration control portion of the circuit via counter U9.

(3) Pulse Duration Control - Pulse duration is determined by the settings of digital switches U20 and U21. These switches produce an 8-bit BCD code which can be multiplexed by U12 and U13 for both control and display purposes. Output from counter U9 is initiated when generator activation is triggered by flip-flop U3. The BCD outputs from U9 are compared to the duration settings from digital switches U20 and U21 by magnitude comparators U10 and U11. When the separate inputs to U10 and U11 are equal (i.e. activation duration has reached the settings on the digital switches) the output from the magnitude comparators and input to OR gate U14 goes high. The output from U14 (and input to U5) goes high, thus reversing the sequence of activation through U5, U6, and U7 as described in section (1) above, clearing flip-flop U3 and deactivating the electrosurgery generator output.

(4) Clock Function Monitoring - To provide some protection in the event that the circuit oscillator or clock, U15, should fail during generator activation, a multivibrator U17 is configured as a retriggered one-shot with the selection of add-on resistance and capacitance values to monitor the output of the oscillator. When the rising edge of each oscillator output pulse is seen within the appropriate time since the previous pulse, U17 is retriggered and the output to U19 remains low. If U17 times out before being retriggered, the output to U19 goes high and will reset the activation flip-flop U3 via AND gate U7, thus deactivating generator output.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method of dividing the cusp in a venous valve using a cuspotome comprising electrically conductive handle means, an electrically conductive arm extending from the handle means, the arm having an outer surface and ending at a hook section which extends laterally from the arm, the hook section terminating at a bulbous member, a blade formed in the hook section adjacent to the bulbous member and electrically insulative material covering the entirety of said outer surface of the arm with the exception being that a portion of the hook section including the blade is free of the insulative material and a portion of said bulbous member which abuts said blade is free of said insulative material, including the steps of:

engaging the cusp of the venous valve with the hook section of the arm; and delivering a pre-selected pulse of electrical current to the blade wherein the blade divides the cusp.

2. The method of claim 1 wherein said step of delivering a pre-selected pulse of electrical current comprises about 30 to about 50 watts.

3. The method of claim 1 including:

immersing the vein in a conductive solution; and gently retroprofusing the vein lumen with a non-conducting isotonic solution.

4. The method of claim 1 including:

controlling the duration of said pre-selected pulse of electrical current.

5. The method of claim 4 wherein:

said duration is about 0.2 to about 0.6 second.

6. The method of claim 1 including:

activating and delivering said pre-selected pulse using a hand or foot manipulated switch means.

* * * * *